(12) United States Patent
Vieira et al.

(10) Patent No.: US 10,801,053 B2
(45) Date of Patent: Oct. 13, 2020

(54) **PROCESS FOR PRODUCING A RHAMNOLIPID PRODUCED BY *PSEUDOMONAS* OR *ENTEROBACTER* USING ANDIROBA OR MURUMURU SEED WASTE**

(71) Applicants: Natura Cosmeticos S/A, Sao Paulo-SP (BR); Instituto de Pesquisas Tecnologicas do Estado de Sao Paulo S.A.-IPT, Sao Paulo-SP (BR)

(72) Inventors: Noemi Jacques Vieira, Sao Paulo-SP (BR); Cintia Rosa Ferrari, Sao Paulo-SP (BR); Gabriela da Silva Bicalho, Hortolandia-SP (BR); Patricia Leo, Sao Paulo-SP (BR); Alfredo Eduardo Maiorano, Sao Paulo-SP (BR); Eliza Mami Ota, Sao Paulo-SP (BR); Maria Filomena de A. Rodrigues, Sao Paulo-SP (BR); Rosa Mitiko Saito Matsubara, Sao Paulo-SP (BR)

(73) Assignees: Natura Cosmeticos S/A, São Paulo (BR); Instituto de Pesquisas Tecnologicas do Estado de Sao Paulo S.A.-IPT, São Paulo (BR)

( * ) Notice: Subject to any disclaimer, the term of this patent is extended or adjusted under 35 U.S.C. 154(b) by 0 days.

(21) Appl. No.: 16/477,496

(22) PCT Filed: Jan. 8, 2018

(86) PCT No.: PCT/BR2018/050003
§ 371 (c)(1),
(2) Date: Jul. 11, 2019

(87) PCT Pub. No.: WO2018/129603
PCT Pub. Date: Jul. 19, 2018

(65) Prior Publication Data
US 2020/0115729 A1 Apr. 16, 2020

(30) Foreign Application Priority Data
Jan. 11, 2017 (BR) .............................. 102017000578

(51) Int. Cl.
*C12P 19/44* (2006.01)
*C12N 1/20* (2006.01)

(52) U.S. Cl.
CPC ................ *C12P 19/44* (2013.01); *C12N 1/20* (2013.01)

(58) Field of Classification Search
CPC ...................................................... C12P 19/44
See application file for complete search history.

(56) References Cited

FOREIGN PATENT DOCUMENTS

| CN | 101898100 A | 12/2010 |
| CN | 104498566 A | 4/2015 |
| EP | 0282942 A2 | 9/1988 |

OTHER PUBLICATIONS

Schmidberger et al., Appl Microbiol Biotechnol., 2014, 98:6725-6737.*
Borges et al., Brazilian J of Chemical Engineering, 2015, 32(2):357-365.*
Lotfabad et al., J Chem Technol Biotechnol., 2016, 91:1368-1377.*
International Searching Authority, International Search Report and Written Opinion for International Application No. PCT/BR2018/050003, dated Feb. 15, 2018, 21 pages, Instituto Macional Da Propriedade Industrial, Brazil.
Mukherjee et al., *Towards Commercial Production of Microbial Surfactants*, Tends in Biotechnology, vol. 24, Issue 11, Nov. 1, 2006, pp. 509-515. DOI: https://doi.org/10.1016/j.tibtech.2006.09.005.
Kumar et al., *Statistical Approach to Optimize Production of Biosurfactant by Pseudomonas Aeruginosa 2297*, 3 Biotech, vol. 5, Issue 1, Feb. 2015, pp. 71-79. DOI: https://doi.org/10.1007/s13205-014-0203-3.
Abalos et al. *Physicochemical and Antimicrobial Properties of New Rhamnolipids Produced by Pseudomonas Aeruginosa AT10 From Soybean Oil Refinery Wastes*, Langmuir, Dec. 6, 2000, vol. 17, No. 5, pp. 1367-1371. DOI: 10.1021/LA00117735.
Benincasa et al. *Pseudomonas Aeruginosa LBI Production as an Integrated Process Using the Wastes From Sunflower-Oil Refining as a Substrate*, ScienceDirect Bioresource Technology, (2008), vol. 99, pp. 3843-3849.
Benincasa, et al., *Rhamnolipid Production by Pseudomonas Aeruginosa LBI Growing on Soapstock as the Sole Carbon Source*, Journal of Food Engineering, Oct. 2002, vol. 54, Issue 4, pp. 283-288. DOI: https://doi.org/10.1016/S0260-8774(01)00214-X.

(Continued)

*Primary Examiner* — Bin Shen
(74) *Attorney, Agent, or Firm* — Alston & Bird LLP

(57) ABSTRACT

Process for producing a rhamnolipid produced by *Pseudomonas* or *Enterobacter* using andiroba or murumuru seed waste, pertaining to the sector of compounds containing monosaccharide radicals, consists of producing rhamnolipids by a biotechnological process using andiroba or murumuru seed waste, following oil extraction, as a substrate for a *Pseudomonas aeruginosa, Enterobacter hormaechei* or *Enterobacter buriae* line cultivated in a bioreactor with a non-dispersive aeration system for reducing foam, producing a rhamnolipid content of 10.5 g/L for *Pseudomonas aeruginosa* bacteria, in bioreactors carried out in a stirred tank with non-dispersive aeration using microporous membranes, particularly of silicone tubes, which allow oxygen to be supplied by diffusion. This type of aeration allows for various configurations, and in the embodiment of the invention, the porous membrane/tube was internally located in the liquid in the bioreactor in the form of a serpentine, under the following process conditions: pure oxygen with suitable pressure and flow rate to maintain O2 pressure in the bioreactor at 20% during the first 24 hours of the assay and stirring varying from 300 to 700 rpm, using 2 radial impellers and manual adjustment according to the decrease in the concentration of dissolved oxygen. The product produced has features that can be used primarily in the cosmetic industry due to its emulsifying, stability and non toxicity capacities.

7 Claims, 4 Drawing Sheets

(56) References Cited

OTHER PUBLICATIONS

Chawala et al., *Rhamnolipid Production by Pseudomonas Aeruginosa Under Denitrification: Effects of Limiting Nutrients and Carbon Substrates*, Biotechnology and Bioengineering, Jan. 5, 2001, vol. 72, No. 1, pp. 25-33. [retrieved from the Internet Sep. 30, 2019] <https://onlinelibrary.wiley.com/doi/abs/10.1002/1097-0290%2820010105%2972%3A1%3C25%3A%3AAID-BIT4%3E3.0.CO%3B2-J>.

Costa et al. *Production of Pseudomonas Aeruginosa LBI Rhamnolipids Following Grown on Brazilian Native Oils*, Process Biochemistry, vol. 41, (2006), pp. 483-488.

Costa. *Produção Biotecnólogica de Surfatante de Bacillus Subtilis Em Residuo Agroindustrial, Caracterização e Aplicações*, Universidade Estadual de Campinas, (2005), (101 pages).

Guerra-Santos et al. *Pseudomonas Aeruginosa Biosurfactant Production in Continuous Culture With Glucose as Carbon Source*, Applied and Environmental Microbiology, Aug. 1984, vol. 48, No. 2, pp. 301-305.

Guerra-Santos et al. *Dependence of Pseudomonas Aeruginosa Continuous Culture Biosurfactant Production on Nutritional and Environmental Factors*, Applied Microbiology and Biotechnology, (1986), vol. 24, pp. 443-448.

Haba et al. *Screening and Production of Rhamnolipids by Pseudomonas Aeruginosa 47T2 NCIB 40044 From Waste Frying Oils*, Journal of Applied Microbiology, (2000), vol. 88, pp. 379-387.

Koch et al. *Genetic Construction of Lactose-tilizing Strains of Pseudomonas Aeruginosa and Their Application in Biosurfactant Production*, Bio/Technology, Nov. 1988, pp. 1335-1339.

Liggett et al. *Corn Steep Liquor in Microbiology*, Bacteriological Reviews, Dec. 1948, vol. 12, No. 4, pp. 297-311.

Makkar et al. *Production of Biosurfactant at Mesophilic and Thermophilic Condictions by a Strain of Bacillus Subtilis*, Journal of Industrial Microbiology & Biotechnology, (1998), vol. 20, pp. 48-52.

Manresa et al. *Kinetic Studies on Surfactant Production by Pseudomonas Aeruginosa 44T1*, Journal of Industrial Microbiology, (1991), vol. 8, pp. 133-136.

Mercadé et al. *Olive Oil Mill Effluent (OOME). New Substrate for Biosurfactant Production*, Bioresource Technology, (1991), vol. 43, pp. 1-6.

Mukherjee et al. *Towards Commercial Production of Microbial Surfactants*, Trends in Biotechnology, Nov. 1, 2006, vol. 24, No. 11, pp. 509-515.

Müller et al. *Evaluation of Rhamnolipid Production Capacity of Pseudomonas Aeruginosa PAO1 in Comparison to the Rhamnolipid Over-Producer Strains DSM 7108 and DSM 2874*, Applied Microbiology and Biotechnology, Feb. 1, 2011, vol. 89, No. 3, pp. 585-592, DOI: 10.1007/s00253-010-2901-z.

Mulligan et al. *Correlation of Nitrogen Metabolism With Biosurfactant Production by Pseudomonas Aeruginosa*, Applied and Environmental Microbiology, Nov. 1989, vol. 55, No. 11, pp. 3016-3019.

Mulligan et al. *The Influence of Phosphate Metabolism on Biosurfactant Production by Pseudomonas Aeruginosa*, Journal of Biotechnology, (1989), vol. 12, pp. 199-210.

Mulligan, *Recent Advances in the Environmental Applications of Biosurfactants*, Current Opinion in Colloid & Interface Science, vol. 14, Issue 5, Oct. 2009, pp. 372-378. DOI: https://doi.org/10.1016/j.cocis.2009.06.005.

Nitschke et al. *Biosurfatantes a Partir de Resíduos Agroindustriais*, Revista Biotecnologia Ciência & Desenvolvimento-Edição n°, Jul. 2003, vol. 31, pp. 63-67.

Nitschke et al. *Oil Wastes as Unconventional Substrates for Rhamnolipid Biosurfactant Production by Pseudomonas Aeruginosa LBI*, Biotechnology Progress, (Jan. 1, 2005), vol. 21, No. 5, pp. 1562-1566.

Ochsner et al. *Isolation and Characterization of a Regulatory Gene Affecting Rhamnolipid Biosurfactant Synthesis in Pseudomonas Aeruginosa*, Journal of Bacteriology, Apr. 1994, vol. 176, No. 7, pp. 2044-2054.

Olvera et al. *The Pseudomonas Aeruginosa algC Gene Product Partipates in Rhamnolipid Biosynthesis*, FEMS Microbiology Letters, (1999), vol. 179, pp. 85-90.

Rahim et al. *Cloning and Functional Characterization of the Pseudomonas Aeruginosa rhlC Gene That Encodes Rhamnosyltransferase 2, An Enzyme Responsible for Di-Rhamnolipid Biosynthesis*, Molecular Microbiology, (2001), vol. 40, No. 3, pp. 708-718.

Ramsay et al. *Production of Poly-(β-Hydroxybutyric-Co-β-Hydroxyvaleric) Acids*, Applied and Environmental Microbiology, Jul. 1990, vol. 56, No. 7, pp. 2093-2098.

Raza et al. *Improved Production of Biosurfactant by a Pseudomonas Aeruginosa Mutant Using Vegetable Oil Refinery Wastes*, Biodegradation, (2007), vol. 18, pp. 1115-1121. DOI: 10.1007/s10532-006-9047-9.

Robert et al. *Effect of the Carbon Source on Biosurfactant Production by Pseudomonas Aeruginosa 44T1*, Biotechnology Letters, (1989), vol. 11, No. 12, pp. 871-874.

Santos et al. *Evaluation of Different Carbon and Nitrogen Sources in Production of Rhamnolipids by a Strain of Pseudomonas Aeruginosa*, In *Biotechnology for Fuels and Chemicals*, (2002), pp. 1025-1035. Humana Press, Totowa, NJ.

Sheppard et al. *The Effects of a Biosurfactant on Oxygen Transfer in a Cyclone Column Reactor*, Journal of Chemical Technology & Biotechnology, (1990), vol. 48, No. 3, pp. 325-336.

Syldatk et al. *Chemical and Physical Characterization of Four Interfacial-Active Rhamnolipids From Pseudomonas Spec. DSM 2874 Grown on n-Alkanes*, Zeitschrift für Naturforschung, Feb. 1, 1985, vol. 40c, Nos. 1-2, pp. 51-60.

Thaniyavarn et al. *Biosurfactant Production by Pseudomonas Aeruginosa A41 Using Palm Oil as Carbon Source*, The Journal of General and Applied Microbiology, (2006), vol. 52, No. 4, pp. 215-222.

Venkata-Ramana et al. *Factors Affecting Biosurfactant Production Using Pseudomonas Aeruginosa CFTR-6 Under Submerged Conditions*, Journal of Chemical Technology & Biotechnology, (1989), vol. 45, No. 4, pp. 249-257.

Yeg et al. *Bioreactor Design for Enhanced Carrier-Assisted Surfactin Production With Bacillus Subtilis*, Process Biochemistry, (2006), vol. 41, pp. 1799-1805.

Hazra et al., *Screening and Identification of Pseudomonas Aeruginosa AB4 for Improved Production, Characterization and Application of a Glycolipid Biosurfactant Using Low-Cost Agro-Based Raw Materials*, J. Chem. Technol. Biotechnol., vol. 86, No. 2, Aug. 17, 2010, pp. 185-198. 10.1002/jctb.2480.

Benincasa et al., *Rhamnolipid Produced From Agroindustrial Wastes Enhances Hydrocarbon Biodegradation in Contaminated Soil*, Current Microbiology, vol. 54, Issue 6, Jun. 2007, pp. 445-449. DOI: https://doi.org/10/1007/s00284-006-0610-8.

\* cited by examiner

PROCESS FOR PRODUCING A RHAMNOLIPID PRODUCED BY *PSEUDOMONAS* OR *ENTEROBACTER* USING ANDIROBA OR MURUMURU SEED WASTE

CROSS REFERENCE TO RELATED APPLICATIONS

This application is a national stage application, filed under 35 U.S. C. § 371, of International Application No. PCT/BR2018/050003, filed Jan. 8, 2018, which claims priority to Brazilian Application No. BR102017000578-0, filed Jan. 11, 2017, the contents of both of which as are hereby incorporated by reference in their entirety.

BACKGROUND

Technical Field

The present invention, which belongs to the field of lipid compounds containing monosaccharide units, refers to biosurfactants/rhamnolipids of microbial origin obtained from *Pseudomonas aeruginosa* or *Enterobacter hormaechei* or *Enterobacter buriae* microbial strains and agroindustrial andiroba or murumuru seed residue as a substrate for their growth and production, and the process for obtaining the same, having features that can be applied in the cosmetics industry due to the emulsifying ability, stability and non-toxicity thereof.

Biosurfactants are surface-active agents having amphipathic (hydrophilic/hydrophobic) characteristics, which are naturally produced and excreted by a wide variety of microorganisms under specific growth conditions. These molecules are classified into glycolipids, phospholipids, lipolipids or lipoproteins.

Glycolipids are low molecular weight biosurfactants, including rhamnolipids (RLs), which act by reducing surface and interfacial tensions, while exhibiting emulsifying, foaming, detergency, wetting and dispersing or solubilizing properties.

Interest in these biosurfactants by the scientific community has grown due to their physicochemical and surfactant properties, which provide them with a wide spectrum of application. Biosurfactants may be used instead of chemically produced, synthetic surfactants as they exhibit less toxicity, are biodegradable and environmentally friendly. Biosurfactants have the potential to be used in different areas such as bioremediation, oil recovery, agriculture (pesticides), pharmaceutical, food industry, dermatology and cosmetics. Thus, rhamnolipids may be used in bioremediation processes, biological control and food and cosmetic industries owing to their good compatibility with the skin and pharmaceuticals. Rhamnolipids have also been used to obtain rhamnose, an important precursor in the production of aromatic compounds.

*Pseudomonas aeruginosa* produces up to six types of rhamnolipids having similar chemical structure and surface activity, reducing the water surface tension from 72 dynes/cm to 30 dynes/cm with a critical micelle concentration of from 27 to 54 mg/L. *P. aeruginosa* is a well-studied strain that mainly produces Rha-C10-C10 type mono-rhamnolipids and Rha2-C10-C10 type di-rhamnolipids.

Biosurfactants from the rhamnolipid class produced by bacteria from the *Pseudomonas* genus had its structure described in the middle of the 40's and since then several authors have presented methods for their production.

DESCRIPTION OF RELATED ART

U.S. Pat. No. 4,628,030 (KAEPELLI, O. AND GUERRA-SANTOS, L. 1986) discloses the first continuous process for producing rhamnolipids by *P. aeruginosa* strain DSM 2659 without using a bioreactor in a culture medium comprising mineral salts and glucose as the carbon source, having limited nitrogen, iron and magnesium availability in order to increase the rhamnolipid concentration thus produced. Said document makes no mention of the use of waste material as raw material/carbon source in the production of rhamnolipids.

Then, document U.S. Pat. No. 4,814,272 (Wagner et al, 1989) disclosed a process for the production of rhamnolipids using different carbon sources and demonstrated that rhamnosyl-$\beta$-hydroxydecanoate and rhamnosyl-rhamnosyl-$\beta$-hydroxydecanoate, in addition to rhamnosyl-$\beta$-hydroxydecanoyl and rhamnosyl-rhamnosyl-$\beta$-hydroxydecanoyl-$\beta$-hydroxydecanoate are also synthesized by *Pseudomonas aeruginosa* strain DSM 2874. The inventors have shown that rhamnolipids containing such chemical structures were produced using glycerin or paraffin as the carbon source and that *Pseudomonas* cells culture temperature also affected their presence. *Pseudomonas* cultures containing glycerin or paraffin at a temperature of 30° C. yielded rhamnolipids containing 16.2 and 17% of the new structures, respectively. When *Pseudomonas aeruginosa* DSM 2874 was cultured at 37° C., the amount of the new chemical structures obtained was 2%. Thus, they have demonstrated that one could modify the rhamnolipid composition in a rather particular condition that involves culture using glycerin or paraffin as the carbon source.

Daniels et al. (EP 0282942, 1988) disclose a method of producing rhamnose via process for producing rhamnolipids using vegetable oils. In the described process, concentrations of the order of 30 to 50 g/L of rhamnolipids are achieved. The main goal of the process is to produce rhamnose, which is obtained by hydrolyzing the rhamnolipid right after its biosynthesis.

In WO 1992005182 (1992), Mixich et al. describe a process for obtaining rhamnose from the hydrolysis of rhamnolipids. Said document focused on the process for hydrolyzing and separating rhamnose from rhamnolipids.

Document U.S. Pat. No. 5,501,966 (Giani et al., 1996) describes the process for producing rhamnose from the hydrolysis of rhamnolipids, resulting from a process using vegetable oils and bacteria from the *Pseudomonas* genus isolated from a water sample or mutants thereof subjected to n-methyl-N-nitro-N-nitrosoguanidine (MNNG). In this process, the rhamnolipid concentration reaches from 70 to 120 g/L.

Chayabutra et al. (CHAYABUTRA, C.; WU, J.; JU, L. K. *Rhamnolipid production by Pseudomonas aeruginosa under denitrification: effects of limiting nutrients and carbon substrates*. Biotechnol Bioeng, v. 72 (1), p. 25-33, 2001) have assessed the rhamnolipid production under denitrification conditions, that is, in the absence of oxygen and in the presence of nitrate as final electron acceptor. In this work fatty acids, vegetable oils, glycerol or glucose were given as the carbon source and limiting cell growth conditions were provided by different nutrients. Phosphorus limitation with was the most effective one for the production of rhamnolipids, resulting in yields four to five times higher than with the conventional nitrogen limitation.

Santos et al (SANTOS, A. S; SAMPAIO, A. P.; VASQUEZ, G. S., SANTA ANNA, L. M.; PEREIRA, N. JR; FREIRE, D. M. *Evaluation of different carbon and nitrogen sources in production of rhamnolipids by a strain of Pseudomonas aeruginosa.* Appl Biochem Biotechnol, v. 98-100, p. 1025-1035) have assessed the rhamnolipid biosynthesis using different carbon (C—glycerol, soybean oil, olive oil and ethanol) and nitrogen (N—$NH_4^+$ and $NO_3^-$) sources, as well as different C/N ratios. The authors have concluded that the relative ratio of rhamnosyl-β-hydroxydecanoyl-β-hydroxydecanoate (mono-rhamnolipid) to rhamnosyl-rhamnosyl-β-hydroxydecanoyl-β-hydroxydecanoate (di-rhamnolipid) varies depending on the carbon source supplied.

The use of hydrophilic (glycerol and glucose) and hydrophobic (soybean grout, frying oil and chicken fat) carbon sources in rhamnolipid production has been studied by Nitschke et al. ((NITSCHKE, M.; COSTA, S. G.; HADDAD, R.; GONÇALVES, L. A.; EBERLEIN, M. N.; CONTIERO, J. *Oil wastes as unconventional substrates for rhamnolipid biosurfactant production by Pseudomonas aeruginosa LBI.* Biotechnol. Prog., 21: 1562-1566, 2005) which found that oily substrates provided a 64% higher rhamnolipid production than non-oily substrates. The study focused on hydrophobic sources as carbon sources showing results equal to or greater than those reported in the literature.

Document EP 0705327-4 A2 (2007) describes a method using selected bacterial strains for the production of rhamnolipids using vegetable oils such as castor, soybean, corn, sunflower, canola, cotton, Jatropha oils and carbohydrates such as glucose, fructose, disaccharides or polysaccharides. In this production method rhamnolipids of varying compositions are obtained in a controlled manner, both as rhamnose/3-hydroxyalkanoates and in the 3-hydroxyalkanoates present therein, by means of a *Pseudomonas aeruginosa* mutant with a defect in the polyhyoxyalkanoate biosynthesis metabolism, thus increasing the spectrum of application thereof in products in bioremediation, food, aroma, cosmetics and pharmaceuticals fields.

Other aspects of rhamnolipid biosynthesis have also been addressed in the literature.

Different genes associated with rhamnolipid biosynthesis have been described: rhlA, rhlB, rhlC, rhlG, rhlR, rhlI, rmlABCD (OCHSNER, U. A.; KOCH, A. K.; FIECHTER, A.; REISER, J. *Isolation and characterization of a regulatory gene affecting rhamnolipid biosurfactant synthesis in Pseudomonas aeruginosa.* J Bacteriol., v. 176(7): 2044-2054, 1994); (RAHIM, R.; OCHSNER, U. A.; OLVERA, C.; GRANINGER, M.; MESSNER, P.; LAM, J. S., SOBERÓN-CHÁVEZ, G. *Cloning and functional characterization of the Pseudomonas aeruginosa rhlC gene that encodes rhamnosyltransferase 2, an enzyme responsible for di-rhamnolipid biosynthesis.* Mol Microbiol 40:708-718, 2001); e Olvera et al., (OLVERA, C.; GOLDBERG, J. B.; SÁNCHEZ, R.; SOBERÓN-CHÁVEZ, G. *The Pseudomonas aeruginosa algC gene product participates in rhamnolipid biosynthesis.* FEMS Microbiol Lett v. 179, p. 85-90 1999). Nucleotide sequences of these genes are available from the *Pseudomonas aeruginosa* genome database PAO1 and PA14 (www.pseudomonas.com).

According to Ochsner and Raiser (OCHSNER, U. A.; KOCH, A. K.; FIECHTER, A.; REISER, J. *Isolation and characterization of a regulatory gene affecting rhamnolipid biosurfactant synthesis in Pseudomonas aeruginosa.* J Bacteriol., v. 176(7):2044-2054, 1994), the main rhamnolipids produced by *Pseudomonas aeruginosa* are rhamnosyl-β-hydroxydecanoyl-β-hydroxydecanoate (mono-rhamnolipid) and rhamnosyl-rhamnosyl-β-hydroxydecanoyl-β-hydroxydecanoate (di-rhamnolipid), however, other chemical structures belonging to the rhamnolipid family have been described.

Interesting examples of biosurfactants of relevance in cosmetic applications are RLs, glycolipids mainly produced by *Pseudomonas aeruginosa* which are readily isolated from the culture medium and can be produced using hydrophobic or hydrophilic substrates such as hydrocarbons, vegetable oils, sugars, glycerol or food industry processing residues. Costa et al., (COSTA, S. G. V. A. O.; NITSCHKE, M, HADDAD; R, EBERLIN M. N.; CONTIERO, J. *Production of Pseudomonas aeruginosa LBI rhamnolipids following growth on Brazilian native oils.* Process Biochemistry, v. 41, p. 483-488, 2006) described the biosynthesis of rhamnolipids by *Pseudomonas aeruginosa* when grown in the presence of 2% by volume of different native Brazilian vegetable oils. Rhamnolipid concentration ranged from 2.9 to 9.9 g/L after 120 hours of cultivation and the mono-rhamnolipid was the main rhamnolipid detected. Rhamnolipid-containing cosmetics have already been patented to be used as anti-wrinkle and anti-aging products (WO1999043334, PILJAC & PILJAC, 1999).

In general, biosurfactants are still unable to compete with synthetic surfactants for commercial purposes owing to their high production and recovery costs. As disclosed by Mukherjeee et al. (MUKHERJEE, S.; DAS, P.; SEN, R. *Towards commercial production of microbial surfactants.* Trends Biotechnol., Amsterdam, 24: 509-515, 2006), three main factors that make the commercialization of biosurfactants difficult are: i) high costs of raw materials; ii) the high recovery and purification costs; and (iii) low yields in the production processes. Thus, several techniques and approaches have been adopted worldwide to reduce biosurfactant production costs and make biosurfactant production more efficient. The alternative use of cheaper substrates, optimized culture conditions in processes carried out in bioreactors, cost effective recovery processes and strain improvements have been investigated to improve biosurfactant productivity.

Thus, the state of the art has demonstrated that bacteria from the *Pseudomonas* genus are able to produce different rhamnolipid family biosurfactants, starting from different substrates, however, there is no information available on the production of rhamnolipids from plant residues. Considering that the substrate used in rhamnolipid production can affect the final product composition and the surfactant properties and, accordingly, the potential applications thereof in addition to the final production costs, the use of agroindustrial residues may provide advantages in terms of costs with raw materials. However, producing biosurfactant molecules having properties applicable to cosmetic products that are similar or superior than those of chemical surfactants is a great challenge.

These alternative nutrient sources, such as agricultural or industrial processing byproducts may reduce the economic burden of biosurfactant production, as raw materials have been estimated to represent about 10 to 30% of the total production costs in many biotechnological processes. In addition, residue reuse may contribute to a reduction in environmental pollution and may enable the economic valuation of residues that would be discarded.

Large residue amounts are generated by the oil and fat industry resulting from both extraction and use of vegetable oils. Studies have shown that vegetable oil residues can be used as substrates for the production of rhamnolipids by some *Pseudomonas aeruginosa* isolates (BENINCASA, M.; CONTIERO, J.; MANRESA, M. A.; MORAES, I. O. *Rhamnohpid production by Pseudomonas aeruginosa LBI growing on soapstock as the sole carbon source*. J. Food Eng., 54: 283-288, 2002); NITSCHKE et al (NITSCHKE, M.; COSTA, S. G.; HADDAD, R.; GONÇALVES, L. A.; EBERLEIN, M. N.; CONTIERO, J. *Oil wastes as unconventional substrates for rhamnolipid biosurfactant production by Pseudomonas aeruginosa LBI*. Biotechnol. Prog., v. 21, p. 1562-1566, 2005); COSTA (COSTA, G. A. N. Produção biotecnológica de surfactante de *Bacillus subtilis* em residuo agroindústria, caracterização e aplicações. 85 p. Master's Degree Dissertation in Food Science; Food Engineering School, Universidade Estadual de Campinas, Campinas, 2005); RAZA et al (RAZA, Z. A.; REHMAN, A.; KHAN, M. S.; KHALID, Z. M. *Improved production of biosurfactant by a Pseudomonas aeruginosa mutant using vegetable oil refinery wastes*. Biodegradation, Dordrecht, v. 18, p. 115-121, 2007). Some authors have also reported the use of sugarcane molasses, cheese, potato and cassava production residues as sources for the production of biosurfactants (MUKHERJEE, S.; DAS, P.; SEN, R. *Towards commercial production of microbial surfactants*. Trends Biotechnol., Amsterdam, 24: 509-515, 2006). Corn steep liquor is a maize grain processing byproduct, being an amino acid-, polypeptide-, mineral- and vitamin-rich acidic material, and may be used as a nutrient supplement in culture media in industrial bioprocesses (LIGGETT R. W.; KOFLER, H. *Corn steep liquor in microbiology*. Bacteriol. Rev., 12: 297-311, 1948). Another alternative source is glycerol, one of the main byproducts obtained in biodiesel production.

Rhamnolipid biosynthesis by *P. aeruginosa* is directly influenced by nutrient availability, since after cell growth, carbon source availability and nitrogen limitation cause increased production of these glycolipids.

The use of hydrophilic (glycerol and glucose) and hydrophobic (soybean grout, frying oil and chicken fat) carbon sources in rhamnolipid production was studied by Nitschke et al. ((NITSCHKE, M.; COSTA, S. G.; HADDAD, R.; GONÇALVES, L. A.; EBERLEIN, M. N.; CONTIERO, J. *Oil wastes as unconventional substrates for rhamnolipid biosurfactant production by Pseudomonas aeruginosa LBI*. Biotechnol. Prog., v. 21, p. 1562-1566, 2005) and found that oily substrates had a 64% higher rhamnolipid production than non-oily substrates. The study focused on hydrophobic sources as carbon sources showing results equal to or greater than those reported in the literature. Nitschke et al (NITSCHKE, M.; COSTA, S. G.; HADDAD, R.; GONÇALVES, L. A.; EBERLEIN, M. N.; CONTIERO, J. *Oil wastes as unconventional substrates for rhamnolipid biosurfactant production by Pseudomonas aeruginosa LBI*. Biotechnol. Prog., v. 21, pp. 1562-1566, 2005) have shown that the studied oily residues are produced in large amounts by vegetable oil and food processing industries, and the use of these residues may contribute not only to the reduction of treatment costs, but also to its economic valuation. Since production costs are the major issue to be overcome for the biosurfactant market to be expanded, the search for alternative substrates and the isolation of new microorganisms represent a strategy to enable the preparation and use of these molecules. These authors' work has shown the potential use of food industry residues as a carbon source in biosurfactant production as well as the isolation of two new microorganisms.

Studies show different types of residues that can be used as alternative substrates in biosurfactant production. Having knowledge on the suitable nutrient composition for cellular growth and buildup of the product of interest is one of the major issues found when selecting the residue to be used. Establishment of a biotechnological process that uses such alternative substrates has also another difficulty, which is the standardization caused by natural variations of the composition, as well as transportation, storage and pre-treatment costs (NITSCHKE, M.; PASTORE, G. M. Biossurfactantes a partir de resíduos agroindustriais: Avaliação de resíduos agroindustriais como substratos para a produção de biossurfactantes por *Bacillus*. Biotecnologia Ciência & Desenvolvimento. 31$^{th}$ edition, page 63-67, June/December 2003), wherein agroindustrial residues have high carbohydrate and lipid levels, showing to be interesting substrates in biosurfactant production (MAKKAR, R. S., CAMEOTRA, S. S. *Production of biosurfactant at mesophilic and thermofilic conditions by a strain of Bacillus subtilis*. Journal of Industrial Microbiology & Biotechnology, 20: 48-52, 1998).

Some authors have already shown the production of rhamnolipids by *Pseudomonas aeruginosa* using unconventional substrates, such as olive oil extraction effluent (MERCADE, M. E.; MANRESA, M. A.; ROBERT, M.; ESPUNY, M. U.; de ANDRES, C.; GUINEA, J. *Olive oil mil efluente (OOME). New substrate for biosurfactant production*. Bioresour. Technol., 43:1-6, 1993), soybean oil refining residues (ABALOS, A.; PINAZO, A.; INFANTE, M. R.; CASALS, M., GARCIA, F.; MANRESA, A. *Physicochemical and antimicrobial properties of new rhamnolipids produced by Pseudomonas aeruginosa AT 10 from soybean oil refinery wastes*. Langmuir, 17: 1367-1371, 2001), whey (KOCH, A. K.; RAISER, J.; KAPPELI, O.; FIECHTER, A. *Genetic construction of lactose utilizing strains of Pseudomonas aeruginosa and their application in biosurfactant production*. Nat. Biotechnol., 6, 1335-1339. doi: 10.1038/nbt 1188-1335, 1988), spent frying oil (HABA E.; ESPUNY M. J.; BUSQUETS M.; MANRESA A. *Screening and production of rhamnolipids by Pseudomonas aeruginosa 47T2 NCIB 40044 from waste frying oils*. J. Appl. Microbiol.; 88: 379-387, 2000).

Thaniyavarn et al. (THANIYAVARN, J.; CHONGCHIN, A.; WANITSUKSOMBUT, N.; THANIYAVARN, S.; PINPHANICHAKARN, P.; LEEPIPATPIBOON, N.; MORIKAWA, M.; KANAYA, S. *Biosurfactant production by Pseudomonas aeruginosa A41 using palm oil as carbon source*. The Journal of General and Applied Microbiology, 52: 215-222, 2006) have found significant differences in yield in rhamnolipid production by *Pseudomonas aeruginosa* strain A41 starting from different carbon sources (2% v/v): olive oil, palm oil, coconut oil, lauric acid, myristic acid, palmitic acid, stearic acid, oleic acid and linoleic acid. The highest bioproduct concentration, i.e., 6.58 g/L, was obtained by culture in olive oil, however, in coconut oil and palm oil, only 2.9 g/L of rhamnolipids were produced.

Manresa et al. (MANRESA, M. A.; BASTIDA, M. E.; MERCADÉ, M R.; DE ANDRÉS, C.; ESPUNY, M. J.; GUINEA, J. *Kinetic studies on surfactant production by Pseudomonas aeruginosa 44T1*. Journal of Industrial Microbiology, 8: 133-136, 1991) consider the rhamnolipid production using olive oil as a complex phenomenon and suggest that *Pseudomonas aeruginosa* 44T1 is likely to produce extracellular lipases that break down triglycerides and catabolize the released fatty acids. They also point out that despite the technical difficulties in the product bioprocess and downstream, rhamnolipid production from vegetable oils has advantages.

Mulligan (MULLIGAN, C. N. *Recent advances in the environmental applications of biosurfactants*. Curr. Op.

Coll. Interf. Sci., 14: 372-378, 2009) have studied *P. aeruginosa* potential to produce rhamnolipids from a wide variety of substrates, including $C_{11}$ and $C_{12}$ alkanes, succinate, pyruvate, citrate, fructose, glycerol, olive oil, glucose and mannitol wherein the rhamnolipid biosurfactant composition and yields also depend on the bioreactor type, pH, nutrient composition, substrate and temperature.

Several authors have employed strategies to optimize the culture medium for biosurfactant production. However, a poorly evaluated factor that may contribute to an increased biosurfactant production is the influence of micronutrients present in the culture medium.

Biosurfactant production faces several processing difficulties. Among the parameters that affect the type and quantity of the formed product are: the carbon source nature, possible nutritional limitations and physical and chemical parameters such as aeration, agitation, foaming, temperature and pH. High C/N ratios (GUERRA-SANTOS, L. H.; KÄPPELI, O.; FIECHTER, A. *Pseudomonas aeruginosa biosurfactant production in continuous culture with glucose as carbon source. Appl Environ Microbiol.*, v. 48, p. 301-305, 1984); e C/P (MULLIGAN C. N.; MAHMOURIDES G., GIBBS B. F. *The influence of phosphate metabolism on biosurfactant production by Pseudomonas aeruginosa*. J Bacteriol 12: 199-210, 1989) stimulate rhamnolipid synthesis whereas high concentrations bivalent cations, particularly iron, are found to be inhibitory (GUERRA-SANTOS, L.; KAPPELI, O.; FIECHTER, A. *Dependence of Pseudomonas aeruginosa continuous culture biosurfactant production on nutritional and environmental factors.* Applied Microbiology and Biotechnology, 24: 443-448, 1986); (BENINCASA, M.; ACCORSINI F. R. *Pseudomonas aeruginosa LBI production as an integrated process using the wastes from sunflower-oil refining as a substrate.* Bioresour. Technol., 99: 3843-3849, 2008) have assessed rhamnolipid production by *P. aeruginosa* LBI under different C/N ratios and reached the highest concentration, 7.3 g/L at a C/N ratio of 8/1. Using $NH_4$, glutamine, asparagine and arginine as a nitrogen source inhibits rhamnolipid production, whereas $NO^3$, glutamate and aspartate promote the synthesis thereof (MULLIGAN, C. N.; GIBBS, B. F. *Correlation of nitrogen metabolism with biosurfactant production by Pseudomonas aeruginosa.* Appl. Environ. Microbiol., 55: 3016-3019, 1989). According to some authors, nitrate is the best nitrogen source to be used, as it stimulates high rhlAB expression, which is the gene sequence responsible for the synthesis of mono-rhamnolipids VENKATARAMANA, K.; KARANTH, N. G. *Factors affecting biosurfactant production using Pseudomonas aeruginosa CFTR-6 under submerged conditions.* J. Chem. Technol. Biotechnol., Oxford, v. 45, p. 249-257, 1989). According to Manresa et al., (MANRESA, M. A.; BASTIDA, M. E.; MERCADÉ, M R.; DE ANDRÉS, C.; ESPUNY, M. J.; GUINEA, J. *Kinetic studies on surfactant production by Pseudomonas aeruginosa 44T1.* Journal of Industrial Microbiology, 8: 133-136, 1991), preference for such nitrogen source may be due to the fact that *P. aeruginosa* is capable of denitrification and, therefore can use nitrate as an electron acceptor even in the presence of oxygen.

Environmental factors and growth conditions such as pH, temperature, agitation and oxygen availability affect biosurfactant production, interfering with growth and cellular activity. Rhamnolipid production by *Pseudomonas* sp. was optimized when the pH was maintained between 6 and 6.5; whereas in a pH greater than 7 the production sharply decreased (GUERRA-SANTOS, L.; KAPPELI, O.; FIECHTER, A. 1984. *Pseudomonas aeruginosa biosurfactant production in continuous culture with glucose as carbon source.* Applied and Environmental Microbiology, 48: 301-305, 1984). The optimal temperature for *P. aeruginosa* 44T1 produce rhamnolipids was 37° C., as shown by Robert et al. ((ROBERT, M.; MERCADÉ, E.; BOSH, M. P.; PARRA, J. L.; ESPUNY; M. J.; MANRESA, M. A.; GUINEA, J. *Effect of the carbon source on biosurfactant production by Pseudomonas aeruginosa 44T1.* Biotechnol. Lett., Dordrecht, v. 1, n. 2, p. 871-874, 1989). Temperature may also affect the composition of the biosurfactant produced by *Pseudomonas* sp. DSM-2874 (SYLDATK, C.; LANG, S.; WAGNER, F. *Chemical and physical characterization of 4interfacial-active rhamnolipids from Pseudomonas spec dsm* 2874 *grown on normal alkanes*. Zeitschrift fur Naturforschung c-a Journal of Biosciences, Tubingen, 40, 51-60, 1985). During yeast production, biosurfactant yield has increased when stirring and aeration rates were high (YEH, M. S.; WEI, Y. H.; CHANG, J. S. *Bioreactor design foe enhanced carrier—assisted surfactin production with Bacillus subtilis.* Proc. Biochem., v. 41, p. 1799-1805, 2006). Para Sheppard e Cooper (SHEPPARD, J. D.; COPPER, D. G. *The effect of biosurfactant on oxygen transfer in acyclone column reactor.* J. Chem. Technol. Biotechnol., Oxford, v. 48, p. 325-336, 1990) oxygen transfer is one of the key parameters for the optimization and large-scale production of surfactin by *B. subtilis*.

Most reports in the literature on the use of agroindustrial products or by-products are related to pure products such as carbohydrates and vegetable oils. Little has been published on the use of solid residues from oleaginous plants (BENINCASA, M.; CONTIERO, J.; MANRESA, M. A.; MORAES, I. O. *Rhamnolipid production by Pseudomonas aeruginosa LBI growing on soapstock as the sole carbon source.* J. Food Eng., v. 54, p. 283-288, 2002) and on possible solutions to foaming issue. MÜLLER et al. have used a foam separator system mounted on the bioreactor head for controlling foaming (MÜLLER, M. M., HÖRMANN, B., KUGEL, M., SYLDATK, C., HAUSMANN, R. *Evaluation of rhamnolipid production capacity of Pseudomonas aeruginosa PAO1 in comparison to the rhamnolipid over-producer strains DSM 7108 and DSM 2874.* Appl Microbiol Biotechnol. v. 89, p. 585-592, 2011.

Novelty and inventive step of the "PROCESS FOR OBTAINING RHAMNOLIPIDS FROM *PSEUDOMONAS AERUGINOSA* USING ANDIROBA SEED RESIDUE" consists of obtaining rhamnolipids by means of a biotechnological process using andiroba seed residues after extraction of andiroba oil as a substrate for the *Pseudomonas aeruginosa* strain, cultured in a bioreactor with a non-dispersive aeration system for foaming reduction, hence obtaining a rhamnolipid content of 10.5 g/L in stirred tank bioreactors with non-dispersive aeration using microporous membranes, particularly silicone tubes, which allow oxygen supply by diffusion. These membranes allow bubble-free aeration to avoid foaming. This type of aeration allows for different configurations to be used, and in the exemplary embodiment of the invention the porous membrane/tube was located internally into the bioreactor liquor in the shape of a coil under the following process conditions: pure oxygen with pressure and flow rate suitable to maintain the $O_2$ pressure in the bioreactor at 20% over the first 24 hours of the assay and stirring speed in the range of from 300 to 700 rpm, using 2 radial impellers and manual configurations made as the dissolved oxygen concentration decreases.

BRIEF SUMMARY

"THE PROCESS for obtaining rhamnolipid from *Pseudomonas* and *Enterobacter* using the ANDIROBA or murumuru seed residue" refers to a process for obtaining rhamnolipid biosurfactant from *Pseudomonas* and *Enterobacter* using andiroba or murumuru seed residue as an alternative and renewable substrate to produce the rhamnolipid biosurfactant, which exhibits emulsifying properties, stability and non-toxicity and finds use in cosmetic formulations, which process comprises the steps of: a) cellular reactivation; b) preparation of an inoculum and c) batch bioprocessing in a bioreactor.

DETAILED DESCRIPTION OF VARIOUS EMBODIMENTS

Figure 1:
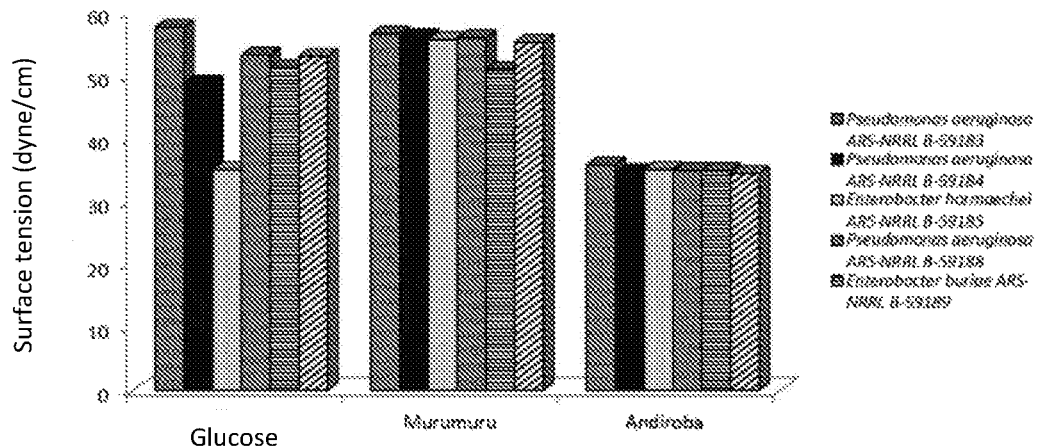
FIG. 1: Plot showing the surface tension of strains Pseudomonas aeruginosa ARS-NRRL B-59183, Pseudomonas aeruginosa ARS-NRRL B-59184, Enterobacter hormaechei ARS-NRRL B-59185, Pseudomonas aeruginosa ARS-NRRL B-59188, Enterobacter buriae ARS-NRRL B-59189 and Pseudomonas aeruginosa ARS-NRRL B-59193 using glucose, murumuru and andiroba.
Figure 2:
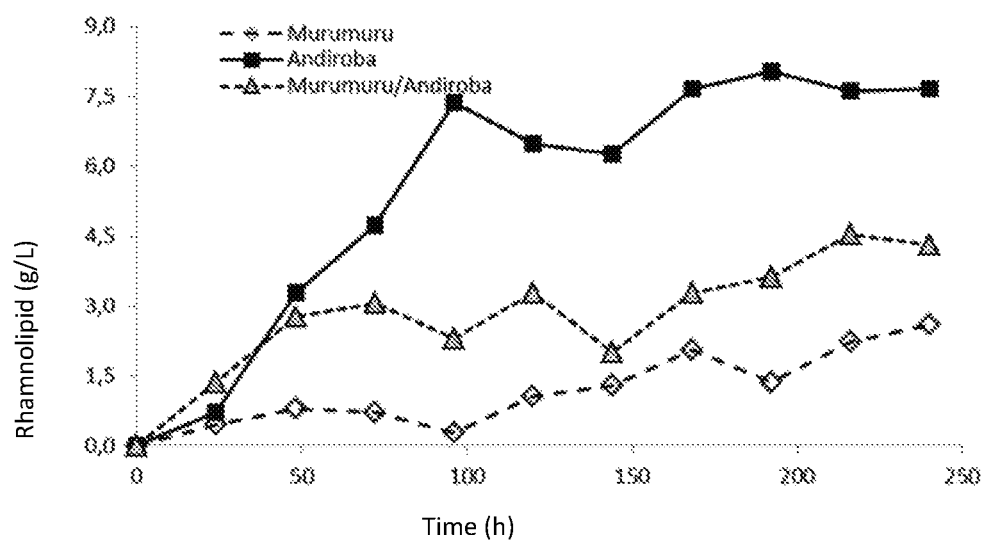
FIG. 2: Plot showing the rhamnolipid production kinetics after daily withdrawals of samples over 240 hours of culture of Pseudomonas aeruginosa in a mineral medium with 10% of androba, murumuru residues or a mixture thereof as growth substrates in a rotary incubator at 180 rpm, 30° C.
Figure 3:
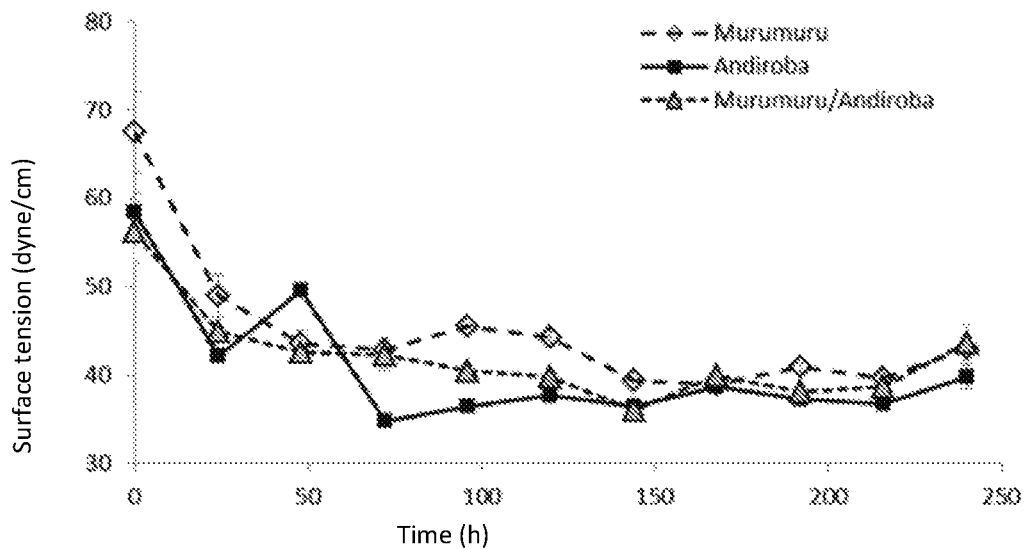
FIG. 3: Plot of the surface tension profile measured in samples withdrawn daily over 240 hours of culture of Pseudomonas aeruginosa in mineral medium with 10% of andiroba, murumuru residues or the mixture thereof as growth substrates in a rotary incubator at 180 rpm, 30° C.
Figure 4:
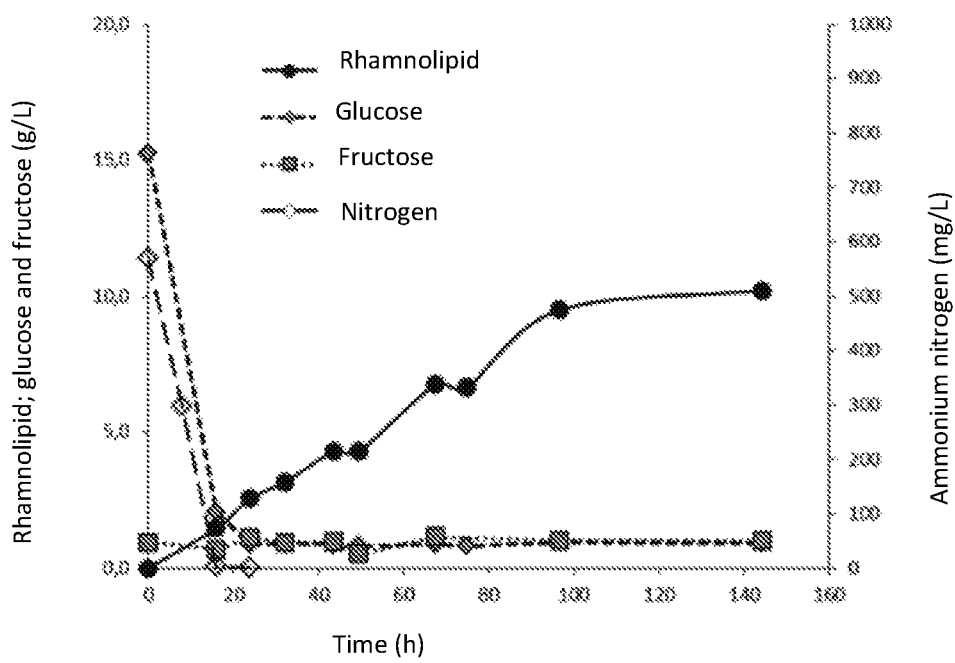
FIG. 4: Plot of rhamnolipid production kinetics in a bioreactor in an oxygen pressure- and pH-controlled bubble-free system in mineral medium with 10% andiroba seed residues and 2% glucose and 3 g/L ammonium sulfate.
Figure 5:
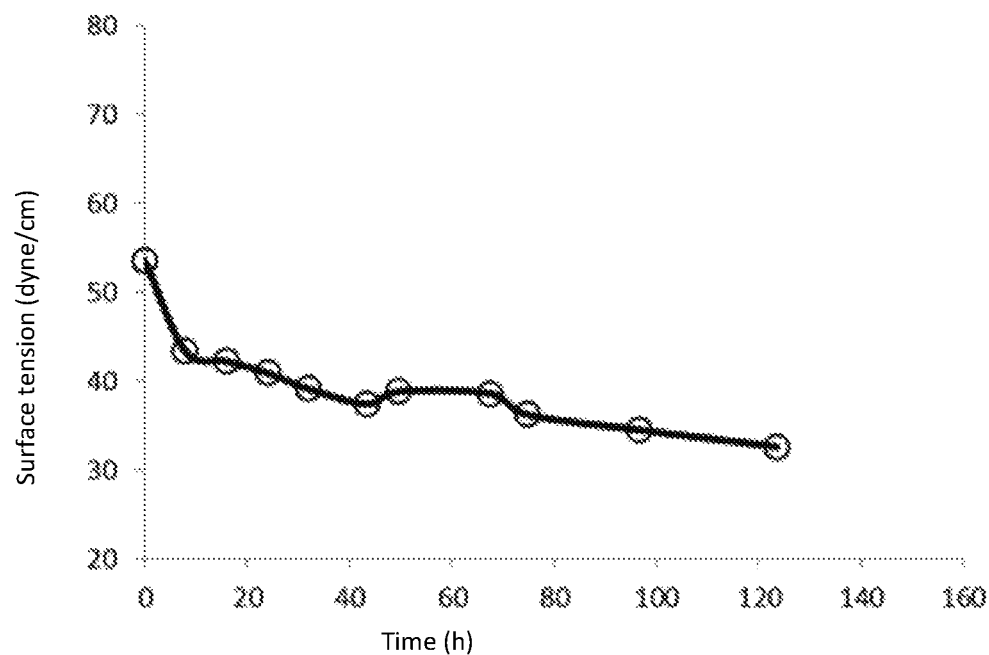
FIG. 5: Plot of the surface tension kinetics in a bioreactor in an oxygen pressure- and pH-controlled bubble-free system in mineral medium with 10% andiroba seed residue and 2% glucose and 3 g/L ammonium sulfate.
Figure 6:
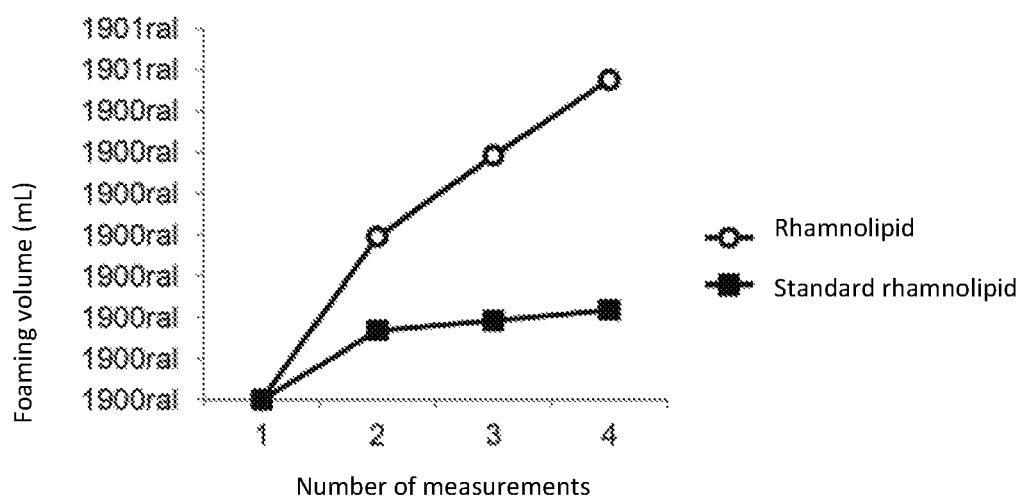
FIG. 6: Plot showing the foaming test comparing the rhamnolipid produced with andiroba seed residue and with commercially available rhamnolipid (Sigma Aldrich).
Figure 7:
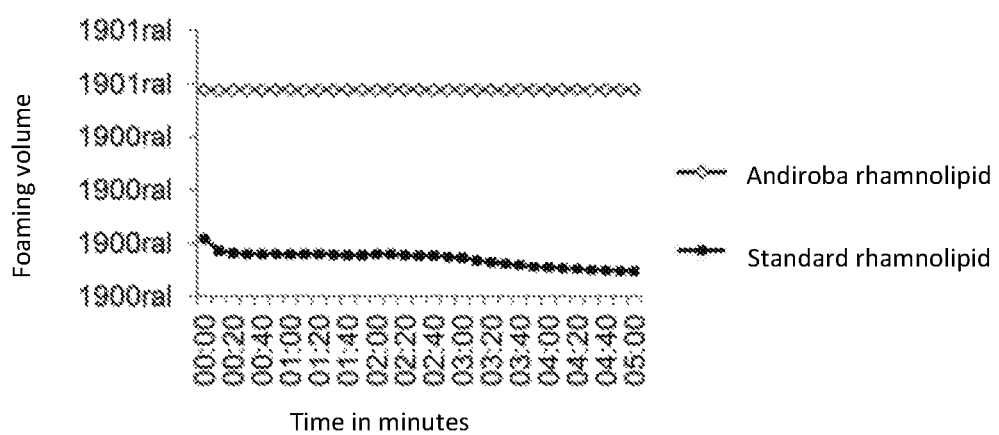
FIG. 7: Plot showing a comparative assessment of foam stability using the rhamnolipid produced with andiroba seed residue and commercially available rhamnolipid (Sigma Aldrich).

Rhamnolipid production is carried out according to the following steps:

step (a) of the process consists of reactivating the microorganism maintained under refrigeration at a temperature of from −70 to −100° C. by means of growth in nutrient broth for 10 to 30 hours, preferably 15 to 25 hours, preferably 21 hours, between 25 and 40° C., preferably at 28° C. and 35° C., more specifically 30° C., on a stirring platform at a stirring speed of 170 rpm to 200 rpm, preferably 180 rpm.

The microorganism of step (a) consists of one of the bacteria listed in Table 1, preferably Pseudomonas aeruginosa, which is preferably kept refrigerated under cryopreservation in ultrafreezer at a temperature of from −70 to −100° C., the nutrient broth preferably comprising 3 g/L meat extract and 5 g/L peptone. These nutrients are mixed with the aid of a magnetic stirrer and subjected to wet heat sterilization at 121° C., 1 atm, for 15 minutes.

Step (b) consists of the preparation of the inoculum, wherein each 1 mL from reactivation step (a) is transferred, preferably in 50 mL of nutrient broth, over 4 to 12 hours, preferably between 6 and 10 hours, more specifically about 8 hours, at a temperature of from 20° C. to 40° C., preferably about 28° C. to 35° C., more specifically at 30° C., on a stirring platform at a stirring speed of from 170-200 rpm, preferably 180 rpm.

Step (c) consists of batch bioprocessing in a stirred tank reactor with aeration, preferably using microporous membranes, more specifically made of silicone tubes that supply oxygen by bubble-free diffusion avoiding foaming.

Such aeration type provides different configurations, preferably the membrane/porous tube being located internally into the bioreactor liquor in the shape of a coil. Pure oxygen is passed through this hose at a suitable pressure and flow rate to maintain the $O_2$ pressure in the bioreactor, preferably at 20% over the first 24 hours. Stirring should be carried out in a range of from 300 to 700 rpm, adjusted as the microorganism grows in order to maintain a 20% $O_2$ saturation at all times using radial impellers and manual or automatic settings being adjusted as the dissolved oxygen concentration decreases, this being a differential of the process over those previously disclosed in the state of the art.

The bioreactor culture of step (c) is carried out in mineral medium consisting of salts and trace elements as per RAMSAY et al. (RAMSAY, B. A.; LOMALIZA, K.; CHAVARIE, C.; DUBE, B.; BATAILLE, P.; RAMSAY, J. A. *Production of Poly-(P-Hydroxybutyric-Co-3-Hydroxyvaleric) Acids.* Applied and Environmental Microbiology, p. 2093-2098 v. 56 (7), 1990) as described in Tables 2A and 2B. The process should be kept constant at a temperature of 28° C. to 37° C., preferably 30° C. and a pH of 6.5 to 7.2, preferably pH 6.8, and may be automatically controlled by addition of NaOH, preferably at 4 mol/L, or by the manual addition of $H_2SO_4$, preferably at 2 mol/L.

TABLE 1

List of bacterial strains used in the steps for producing rhamnolipid.

| Strain name | Bank of Origin and registration number | IPT number |
|---|---|---|
| Pseudomonas aeruginosa (Schroeter 1872) Migula 1900 E03-31 | ARS-NRRL B-59183 | 998 |
| Pseudomonas aeruginosa (Schroeter 1872) Migula 1900 E03-36 | ARS-NRRL B-59184 | 999 |
| Enterobacter hormaechei O'Hara et al. 1990E03-50 | ARS-NRRL B-59185 | 1000 |
| Pseudomonas aeruginosa (Schroeter 1872) Migula 1900H05-11 | ARS-NRRL B-59188 | 1001 |
| Enterobacter buriae Brenner et al. 1988 H05-14 | ARS-NRRL B-59189 | 1002 |
| Pseudomonas aeruginosa (Schroeter 1872) Migula 1900 H05-45 | ARS-NRRL B-59193 | 1005 |

TABLE 2A

Composition of the mineral medium used for growth and rhamnolipid production.

| Mineral medium components | Concentration (g/L) |
|---|---|
| Dibasic sodium phosphate ($Na_2HPO_4$) | 3.5 |
| Potassium phosphate ($KH_2PO_4$) | 1.5 |
| Ammonium sulfide ($(NH_4)_2SO_4$) | 1.0 to 3.0 |
| Magnesium sulfide ($MgSO_4 \cdot 7H_2O$) | 0.2 |
| Calcium chloride ($CaCl_2 \cdot 2H_2O$) | 0.01 |
| Ammonium iron(III) citrate | 0.06 |
| Solution of trace elements (Table 3) | 1.0 mL |
| Glucose | 0 to 2.0 |
| Andiroba solid residue | 100 |
| Distilled $H_2O$ | q.s.p. 1 L |

TABLE 2B

Composition of the trace element solution

| Components of the trace element solution | Concentration (g/L) |
|---|---|
| Boric Acid ($H_3BO_3$) | 0.3 |
| Cobalt chloride ($CoCl_2 \cdot 6H_2O$) | 0.2 |
| Zinc sulfate ($ZnSO_4 \cdot 7H_2O$) | 0.1 |
| Manganese chloride ($MnCl_2 \cdot 4H_2O$) | 0.03 |
| Sodium molybdate ($NaMoO_4 \cdot 2H_2O$) | 0.03 |
| Nickel chloride ($NiCl_2 \cdot 6H_2O$) | 0.02 |
| Copper sulfide ($CuSO_4 \cdot 5H_2O$) | 0.01 |
| Distilled $H_2O$ | q.s.p. 1 L |

All strains listed in Table 1 exhibited rhamnolipid production using murumuru and andiroba seed residues, evidencing that they can be used to obtain surfactant.

From among the assessed strains all of them exhibited similar surface tension results using both andiroba and murumuru seed residues.

Rhamnolipid production is carried out according to the following steps:

Step (a) of the process consisted of reactivating *Pseudomonas aeruginosa*, or *Enterobacter hormaechei* or *Enterobacter buriae* over 21 hours at a temperature of 30° C. on a stirring platform at a stirring speed of 180 rpm, the nutrient broth containing meat extract and peptone at 3 g/L and 5 g/L, respectively.

Step (b) consisted of preparing the inoculum, wherein each 1 mL from reactivation step (a) was inoculated into 50 mL of the nutrient broth for about 8 hours at a temperature of 30° C. on a stirring platform at a stirring speed of 180 rpm.

Step (c) consisted of a batch bioprocessing in a stirred tank reactor under aeration by means of silicone tubes that allowed the supply of pure oxygen by bubble-free diffusion, at suitable pressure and flow rate to maintain the $O_2$ pressure at 20% over the first 24 hours, hence avoiding foaming. Stirring at 300 rpm to 700 rpm in the reactor was carried out by radial impellers and the dissolved oxygen concentration decrease was manually set.

The process was kept constant at a temperature of 30° C. and a pH of 6.8, being controlled by the addition of 4 mol/L NaOH, or by 2 mol/L $H_2SO_4$.

Andiroba and murumuru residues used in the tests were pre-ground using a domestic food processor at 10-second pulses or an industrial blender equipped with a high rotation stainless steel cup (22,000 rpm) and a power of 1200 w. After grinding, when necessary, the residues were sifted through a set of sieves ranging from 1.0 to 0.25 mm.

Results

The *Pseudomonas aeruginosa* strain was able to synthesize about 10 g/L rhamnolipid from ground andiroba residues used as an alternative substrate at a concentration of 100 g/L.

Rhamnolipid production using andiroba seed residue was about 4 times higher than the production using murumuru seed residue. Surface tension of the culture supernatant with andiroba seed residue (<35 dynes/cm) was also better than the tension obtained with murumuru seed residue (>35 dynes/cm).

Andiroba and murumuru seed residues were characterized with respect to their composition, showing the presence of carbohydrates, lipids and proteins in both residues. The murumuru seed residue exhibited 53.4% carbohydrates, 29.0% lipids and 6.8% proteins. The andiroba seed residue exhibited 63.4% carbohydrates, 14.8% lipids and 10.4% proteins. Other components such as ash and moisture were also quantified, wherein 1.4% ash was found in murumuru seed residue and 4.3% ash in andiroba seed residue.

The rhamnolipid biosurfactant molecule produced using andiroba seed residue had a surface tension of from 30 to 40 dynes/cm and an emulsification index greater than 60%. With murumuru residue, the surface tension obtained was 40 to 50 dynes/cm and the emulsification index was also greater than 60%.

The produced rhamnolipid did not present any cytotoxicity in in vitro assays and exhibited good performance in terms of surfactant and foaming properties. Said performance was measured in an apparatus that evaluates the foaming ability of surfactant-containing solutions via stirring and assessing stability of the foam obtained after stirring. The average foaming values are obtained after four foam decay readings for five minutes. In this evaluation a corrected concentration of surfactants was used considering a sample content to 0.1% of active. Tests were made using the rhamnolipid produced in a bioreactor and dried in a freeze-drying equipment versus Sigma Aldrich standard rhamnolipid.

The average foaming results for rhamnolipids produced with andiroba seed residue were shown to be better than those obtained using Sigma Aldrich standard rhamnolipid.

Rhamnolipid foam stability was shown to very good when compared to the rhamnolipid standard, which makes the product interesting to be applied in cosmetics as it maintains the foam stable over the course of the analysis.

The rhamnolipid molecule was also shown to be quite stable, which means that the produced biosurfactant can be applied in the cosmetic industry due to its in vitro emulsifying ability, stability and non-toxicity.

The invention claimed is:

1. A process for obtaining rhamnolipid from *Pseudomonas* or *Enterobacter* using andiroba or murumuru seed residue, comprising the following steps:
   (a) reactivating the microorganism kept under refrigeration by means of growth in nutrient broth;
   (b) preparing an inoculum; and
   (c) batch bioprocessing in a stirred tank reactor under aeration conditions,
   wherein:
   step a) reactivates *Pseudomonas* or *Enterobacter* microorganisms kept under cryopreservation refrigeration at a temperature ranging from −70 to −100° C., by growing in a nutrient broth for 10 to 30 hours, at a temperature of from 25 to 40° C., on a stirring platform at a stirring speed of 170 rpm to 200 rpm, the nutrient broth comprising meat extract and peptone, which nutrients are mixed with the aid of a stirrer and are subjected to wet heat sterilization at 121° C., 1 atm, for 15 minutes;
   step (b) consists of preparing the inoculum by transferring the material from reactivation step (a) to a nutrient broth for 4 to 12 hours at a temperature between 20° C. to 40° C. on a stirring platform at a stirring speed of from 170 to 200 rpm;
   step (c) consists of batch bioprocessing the prepared inoculum of step (b) and the andiroba or murumuru seed residue in a stirred tank reactor at 300 to 700 rpm under aeration with microporous membranes through which pure oxygen at an adequate pressure and flow rate is passed to maintain the $O_2$ pressure in the bioreactor at 20% over the first 24 hours, wherein stirring settings should be varied as the microorganism grows, in order to maintain 20% $O_2$ saturation at all times by using radial impellers and manual or automatic settings as the oxygen concentration decreases, hence keeping the process constant at a temperature of 28° C. to 37° C., and pH 6.5 to 7.2, the mineral medium of this step comprising salts and trace elements.

2. The process for obtaining rhamnolipid from *Pseudomonas* or *Enterobacter* using andiroba or murumuru seed residue according to claim 1, wherein:
step (a) consists of reactivating the microorganisms in nutrient broth for 15 to 25 hours at a temperature between 28° C. and 35° C. on a stirring platform at a stirring speed of 180 rpm and wherein the nutrient broth comprises 3 g/L meat extract and 5 g/L peptone;
step (b) consists of preparing the inoculum by transferring 1 mL of the material of step (a) into 50 mL of nutrient broth for 6 and 10 hours at a temperature between 28° C. to 35° C. on a stirring platform at a stirring speed of 180 rpm;
step (c) consists of batch bioprocessing the prepared inoculum of step (b) and the andiroba or murumuru seed residue in a stirred tank reactor under aeration with microporous membranes of silicone tubes located internally into the bioreactor liquor in the shape of a coil, the process being maintained at a temperature of 30° C. and pH 6.8 and being controllable by the addition of 4 mol/L NaOH or addition of 2 mol/L $H_2SO_4$.

3. The process for obtaining rhamnolipid from *Pseudomonas* or *Enterobacter* using andiroba or murumuru seed residue according to claim 1, wherein:
step (a) consists in reactivating the microorganism in nutrient broth for 21 hours at a temperature of 30° C.; and
step (b) consists of preparing the inoculum by transferring the material from step (a) into the nutrient broth for 8 hours at 30° C.

4. The process for obtaining rhamnolipid from *Pseudomonas* or *Enterobacter* using andiroba or murumuru seed residue according to claim 1, wherein it uses *Pseudomonas aeruginosa* ARS-NRRL B-59183 or ARS-NRRL B-59184 or ARS-NRRL B-59188 or ARS-NRRL B-59193; or *Enterobacter hormaechei* ARS-NRRL B-59185 or *Enterobacter buriae* ARS-NRRL B-59189 bacteria.

5. The process for obtaining rhamnolipid from *Pseudomonas* or *Enterobacter* using andiroba or murumuru seed residue according to claim 1, wherein *Pseudomonas aeruginosa* ARS-NRRL B-59183 or ARS-NRRL B-59184 or ARS-NRRL B-59188 or ARS-NRRL B-59193 bacteria are used.

6. The process for obtaining rhamnolipid from *Pseudomonas* or *Enterobacter* using andiroba or murumuru seed residue, according to claim 1, wherein the bioreactor culture of step (c) is carried out in mineral medium comprising 3.5 g/L dibasic sodium phosphate ($Na_2HPO_4$), 1.5 g/L potassium phosphate ($KH_2PO_4$), 1.0 to 3.0 g/L ammonium sulfide ($(NH_4)_2SO_4$), 0.2 g/L magnesium sulfide ($MgSO_4.7H_2O$), 0.01 g/L calcium chloride ($CaCl_2.2H_2O$); 0.06 g/L ammonium iron(III) citrate, 0 a 2.0 g/L glucose, 100 g/L solid Andiroba residue, 1.0 ml/g/L trace element solution, q.s.p. 1 L distilled $H_2O$; and the trace element solution comprising 0.3 g/L boric Acid ($H_3BO_3$), 0.2 cobalt chloride ($CoCl_2.6H_2O$); 0.1 zinc sulfate ($ZnSO_4.7H_2O$), 0.03 g/L manganese chloride ($MnCl_2.4H_2O$), 0.03 g/L sodium molybdate ($NaMoO_4.2H_2O$), 0.02 g/L nickel chloride ($NiCl_2.6H_2O$), 0.01 g/L copper sulfate ($CuSO_4.5H_2O$), q.s.p. 1 L Distilled $H_2O$.

7. The process for obtaining rhamnolipid from *Pseudomonas* or *Enterobacter* using andiroba or murumuru seed residue, according to claim 1, wherein the used andiroba and murumuru residues are pre-ground and, after grinding, when necessary, the residues are sifted through a set of sieves ranging from 1.0 to 0.25 mm.

* * * * *